US009345566B2

(12) United States Patent
Bosel

(10) Patent No.: US 9,345,566 B2
(45) Date of Patent: May 24, 2016

(54) DELIVERY DEVICE AND SYSTEM FOR OPEN SURGICAL REPAIR

(71) Applicant: Cook Medical Technologies LLC, Bloomington, IN (US)

(72) Inventor: Christopher D. Bosel, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 709 days.

(21) Appl. No.: 13/627,428

(22) Filed: Sep. 26, 2012

(65) Prior Publication Data

US 2014/0088677 A1  Mar. 27, 2014

(51) Int. Cl.
*A61B 17/08* (2006.01)
*A61F 2/06* (2013.01)
*A61B 17/11* (2006.01)

(52) U.S. Cl.
CPC .............. *A61F 2/064* (2013.01); *A61B 17/11* (2013.01); *A61B 2017/1107* (2013.01); *A61B 2017/1125* (2013.01); *A61B 2017/1132* (2013.01)

(58) Field of Classification Search
CPC  A61F 2/064; A61B 2017/1132; A61B 17/11; A61B 2017/1107; A61B 2017/1125
USPC ................ 606/108, 205–209; 623/1.11, 1.12, 623/1.13, 2.11, 1.23
See application file for complete search history.

(56) References Cited

U.S. PATENT DOCUMENTS

| | | | |
|---|---|---|---|
| 5,591,226 A * | 1/1997 | Trerotola ............... | A61B 17/11 606/108 |
| 6,168,623 B1 * | 1/2001 | Fogarty ................. | A61B 17/11 623/1.1 |
| 7,766,953 B2 | 8/2010 | Purdy et al. ................. | 623/1.12 |
| 2002/0123786 A1 * | 9/2002 | Gittings ........... | A61B 17/00234 623/1.11 |
| 2003/0220661 A1 * | 11/2003 | Mowry ................. | A61B 17/11 606/153 |
| 2007/0027526 A1 | 2/2007 | Demetriades et al. ....... | 623/1.13 |
| 2007/0198077 A1 | 8/2007 | Cully et al. ................. | 623/1.12 |
| 2009/0254168 A1 | 10/2009 | Parker et al. ................. | 623/1.11 |
| 2012/0035706 A1 | 2/2012 | Paul, Jr. et al. ............... | 623/1.12 |
| 2012/0035708 A1 | 2/2012 | Paul, Jr. et al. ............... | 623/1.16 |
| 2012/0123511 A1 | 5/2012 | Brown ......................... | 623/1.11 |
| 2012/0271400 A1 | 10/2012 | Lyons et al. ................. | 623/1.12 |
| 2012/0271402 A1 | 10/2012 | Sargent, Jr. .................. | 623/1.15 |

FOREIGN PATENT DOCUMENTS

JP   2002-253553   *   9/2002

OTHER PUBLICATIONS

Machine Translation of JP 2002-253553, translated on Aug. 24, 2015, pp. 1-7.*

* cited by examiner

*Primary Examiner* — Jing Ou
(74) *Attorney, Agent, or Firm* — Brinks Gilson & Lione

(57) ABSTRACT

A device for delivering a prosthesis to a damaged body vessel includes first and second generally elongated members joined to each other along a length thereof. A distal end of each of the elongated members is insertable through an outer layer of skin to access the vessel. The distal ends are cooperatively maneuverable between a closed position for retaining the prosthesis during delivery to the vessel and an open position for releasing the prosthesis upon delivery. Each of the elongated members has a prosthesis retaining member disposed at a distal tip. The retaining members are configured for retaining the prosthesis in a constricted condition when the distal ends are in the closed condition for delivery of the prosthesis to the damaged vessel.

8 Claims, 3 Drawing Sheets

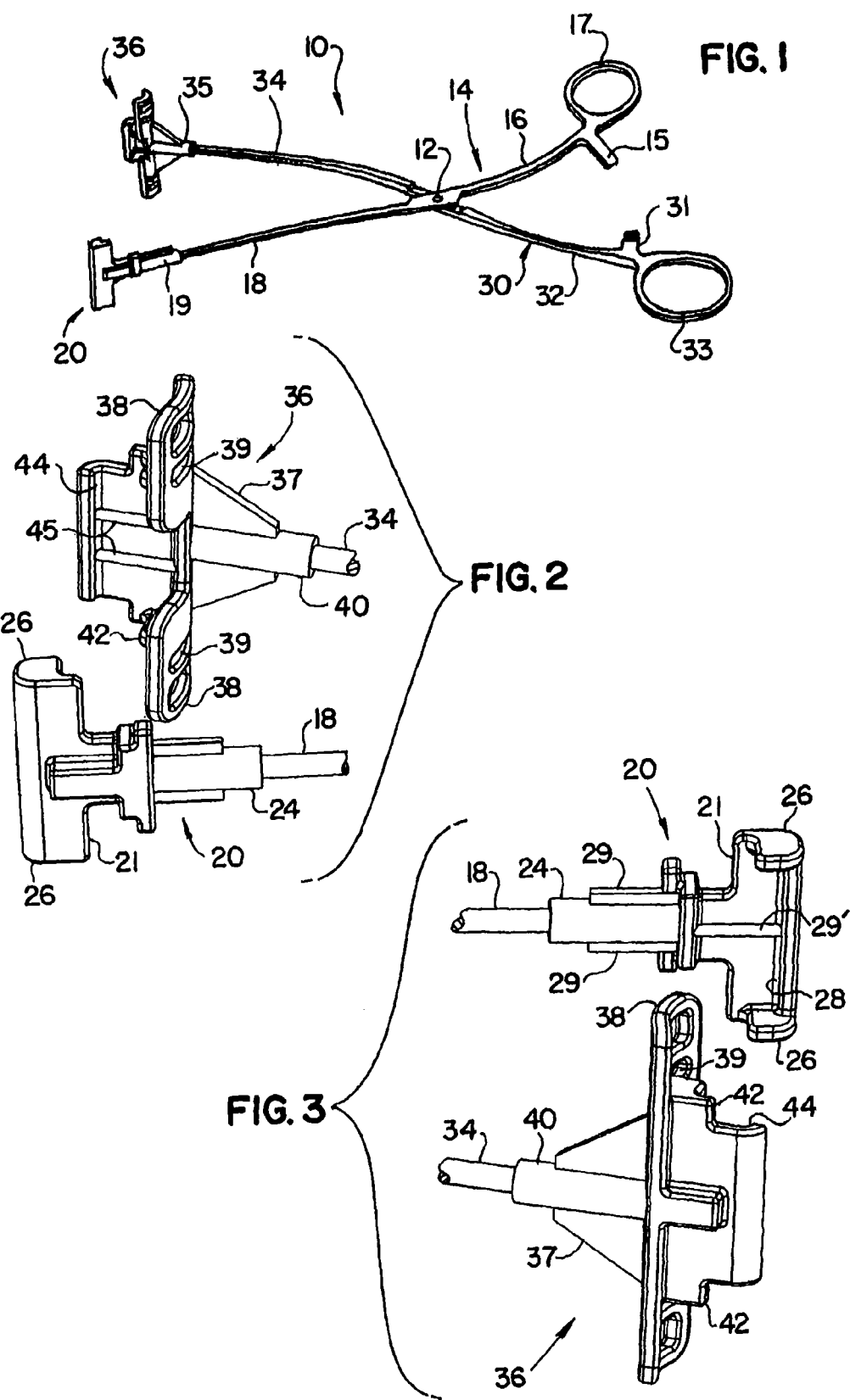

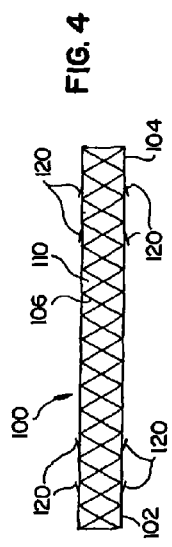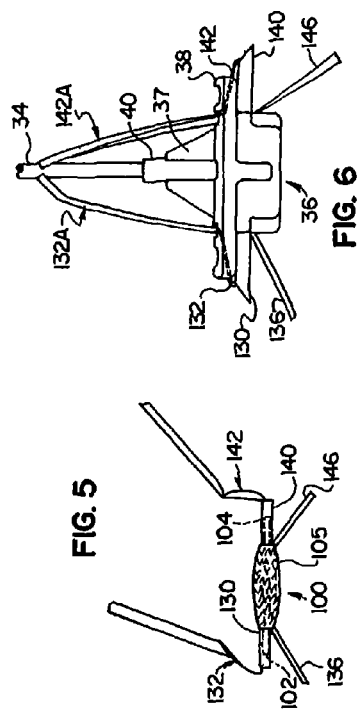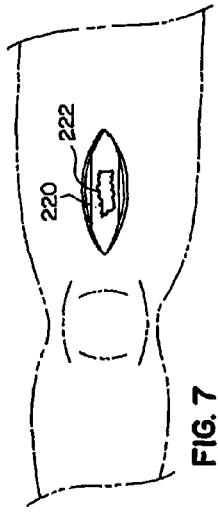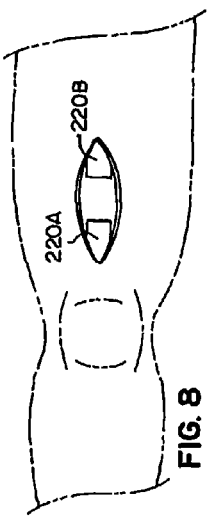

DELIVERY DEVICE AND SYSTEM FOR OPEN SURGICAL REPAIR

BACKGROUND

1. Technical Field

The preferred embodiments described herein relate generally to devices for delivering a medical interventional device for repair of body structures that define body lumens. More particularly, they relate to delivery devices for delivering expandable prostheses and like devices for repairing damaged body structures and gaining hemostasis or fluid stability during emergency open surgical medical procedures.

2. Background Information

Trauma physicians frequently encounter patients having traumatic injury to a body vessel, such as lacerated vessels or even transected vessels, resulting from gunshots, knife wounds, motor vehicle accidents, explosions, etc. Significant damage to a body vessel may expose a patient to deleterious conditions such as the loss of a limb, loss of function of a limb, increased risk of stroke, impairment of neurological functions, and compartment syndrome, among others. Particularly severe cases of vascular injury and blood loss may even result in death. In such severe situations, the immediate goal is to obtain hemostasis while maintaining perfusion of adequate blood flow to critical organs, such as the brain, liver, kidneys, and heart.

Examples of treatment that are commonly performed by trauma physicians to treat body vessel injuries include the clamping of the vessel with a hemostat, the use of a balloon tamponade, the ligation of the damaged vessel at or near the site of injury, and/or the insertion of one or more temporary shunts. However, conventional surgical repair is generally difficult with actively bleeding, moribund patients. In many instances, there is not enough time to repair the body vessel adequately by re-approximating and suturing the body vessel. Thus, the trauma physician may simply insert a temporary shunt into the vessel. However, use of temporary shunts has been linked to the formation of clots. This may require returning the patient to the operating room for treatment and removal of the clots, often within about 36 to 48 hours of the original repair. Since such shunts are generally placed as a temporary measure to restore blood flow and stop excessive blood loss, the shunt is typically removed by a specialized vascular surgeon once the patient has stabilized (generally a few days later). After removal, the vascular surgeon will typically replace the shunt with a vascular graft, such as a fabric graft that is sewn into place. With respect to ligation, ligation of the damaged blood vessel may result in muscle necrosis, loss of muscle function, or a potential limb loss or death.

Due to the nature of the body vessel injury that may be encountered, the insertion of shunts or ligation of a blood vessel, for example, often requires that such treatments be performed within a very short period of time. Such treatments may occupy an undue amount of time and attention of the trauma physician at a time when other pressing issues regarding the patient's treatment require immediate attention. In addition, the level of particularized skill required to address a vascular trauma and stabilize the patient may exceed that possessed by the typical trauma physician.

Some open surgical techniques utilize sutures to affix damaged tissue portions to fittings that have been deployed with the vessel. Such techniques require the trauma physician to take sufficient time to tie the sutures properly. Even though in modern medicine sutures can be tied in relatively rapid fashion, any step in a repair process that occupies physician time in an emergency situation is potentially problematic. In addition, the use of sutures to affix the vessel to the fitting compresses the tissue of the vessel against the fitting. Compression of tissue may increase the risk of necrosis of the portion of the vessel tissue on the side of the suture remote from the blood supply. When present, necrosis of this portion of the vessel tissue may result in tissue separation at the point of the sutures. In this event, the connection between the vessel and the fitting may eventually become weakened and subject to failure. If the connection fails, the device may disengage from the vessel. Therefore, efforts continue to be made to develop suitable techniques that reduce the physician time required for such repair, so that this time can be spent on other potentially life-saving measures, and so that the blood flow may be more quickly restored and any resulting damage caused by lack of blood flow is minimized.

What is needed is a device for delivering a prosthesis for repair of a damaged body vessel, such as an artery or a vein, (and in particular a transected vessel) during emergency open surgery. It would be desirable if the delivery device was easy for a trauma physician to use, and was useful for the rapid introduction of a prosthesis into a body vessel, thereby providing a conduit for blood or fluid within the damaged body vessel.

BRIEF SUMMARY

The problems of the prior art are addressed by the features of the present invention. In one aspect, a device for delivering a prosthesis to a damaged body vessel is disclosed, wherein the prosthesis is of a type having a constricted condition for delivery to the damaged body vessel, and an expanded condition upon deployment at the damaged vessel. First and second generally elongated members are joined to each other along a respective length thereof. Each of the elongated members has a proximal end accessible to an operator during use of the device, a distal end for insertion through a body opening from an outer layer of skin to access the damaged body vessel, and a pivot point intermediate the proximal and distal ends along the length for joinder to the other elongated member. The elongated members are arranged along the pivot point such that the respective distal ends are cooperatively maneuverable between a closed position for retaining the prosthesis during a delivery to the damaged body vessel and an open position for releasing the prosthesis upon the delivery. The first elongated member has a first prosthesis retaining member disposed at the distal tip thereof, and the second elongated member has a second prosthesis retaining member disposed at the distal tip thereof. The first and second prosthesis retaining members are configured for retaining the prosthesis therebetween in the constricted condition when the distal ends are in the closed condition for delivery of the prosthesis at the damaged vessel.

In another aspect, a system for open surgical repair of a damaged wall portion of a body vessel is disclosed. A prosthesis has a first end and a second end. The prosthesis is expandable from a constricted condition wherein at least the first and second ends have a diameter less than a diameter of the body vessel at the damaged wall portion, to an expanded condition wherein the prosthesis ends engage an interior surface of the body vessel. A first splittable sheath maintains the prosthesis first end in the constricted condition, and a second splittable sheath maintains the prosthesis second end in the constricted condition. Each of the sheaths has a tab extending therefrom, and is configured for splitting upon a withdrawal of the tab such that the respective prosthesis end is expandable from the constricted condition to the expanded condition. A delivery device is provided for delivery of the prosthesis to the damaged wall portion. The delivery device comprises first and second generally elongated members, wherein each elongated member has a proximal end accessible to an operator, and a distal end for insertion through the damaged wall portion. The elongated members are joined at a pivot point such that the distal ends are maneuverable between a closed position for retaining the prosthesis during delivery to the damaged wall portion, and an open position for releasing the prosthesis upon deployment at the damaged wall portion. The first elongated member has a first retaining member disposed at the first elongated member distal end, and the second elongated member has a second retaining member disposed at the second elongated member distal end. The first and second retaining members are configured for retaining the prosthesis therebetween in the constricted condition for insertion through the damaged wall portion when the distal ends are arranged in the closed position.

In yet another aspect, a method for open surgical repair of a damaged portion of a body vessel is disclosed. A device having a prosthesis assembly loaded therein is positioned for delivery to the damaged vessel portion through an open air pathway. The device comprises first and second generally elongated members, wherein each generally elongated member has a proximal end accessible to an operator, a distal end for insertion to the damaged vessel portion, and is joined to the other elongated member along a length thereof. Each of the distal ends extends to a distal tip. The first elongated member has a first prosthesis retaining member disposed at the first elongated member distal tip, and the second elongated member has a second prosthesis retaining member disposed at the second elongated member distal tip. The elongated members are arranged such that the distal ends are cooperatively maneuverable between a closed position having the prosthesis assembly loaded therein, and an open position. The prosthesis assembly comprises a prosthesis having first and second ends, and respective first and second sheaths configured for maintaining the first and second prosthesis ends in a constricted condition. Each of the first and second sheaths includes a tab member for selectively splitting the sheath. The distal ends of the device are passed through the open air pathway to the damaged vessel portion with the distal ends in the closed position. The distal ends are maneuvered such that the first sheath and the first constricted prosthesis end are inserted into a first side of the damaged vessel portion, and such that the second sheath and the second constricted prosthesis end are inserted into a second side of the damaged vessel portion. The first sheath tab member is pulled for splitting the first sheath, wherein the first prosthesis end expands to engage an inner surface of the first side of the damaged vessel portion. The second sheath tab member is pulled for splitting the second sheath, wherein the second prosthesis end expands to engage an inner surface of the second side of the damaged vessel portion.

BRIEF DESCRIPTIONS OF THE DRAWINGS

FIG. 1 illustrates one example of a delivery device for delivering a prosthesis for implantation within a body vessel;

FIG. 2 is an enlarged view of the distal end of the delivery device, illustrating the retaining members of the delivery device in an open position;

FIG. 3 is another enlarged view of the distal end of the delivery device, with the retaining members in an opposite rotational orientation when compared to the orientation of FIG. 2;

FIG. 4 is a side view of one example of a radially expanded prosthesis suitable for deployment at a target site by the delivery device of FIG. 1;

FIG. 5 is a side view of the prosthesis in condition for deployment, wherein each end of the prosthesis is constricted in a splittable sheath;

FIG. 6 is a side view of the prosthesis of FIG. 5 loaded into a delivery device for deployment;

FIG. 7 illustrates a leg of a patient that has been opened to expose a damaged body vessel;

FIG. 8 illustrates the body vessel of FIG. 7, wherein the vessel has been cut into two end portions;

DETAILED DESCRIPTION OF THE DRAWINGS AND THE PRESENTLY PREFERRED EMBODIMENTS

Figure 9:
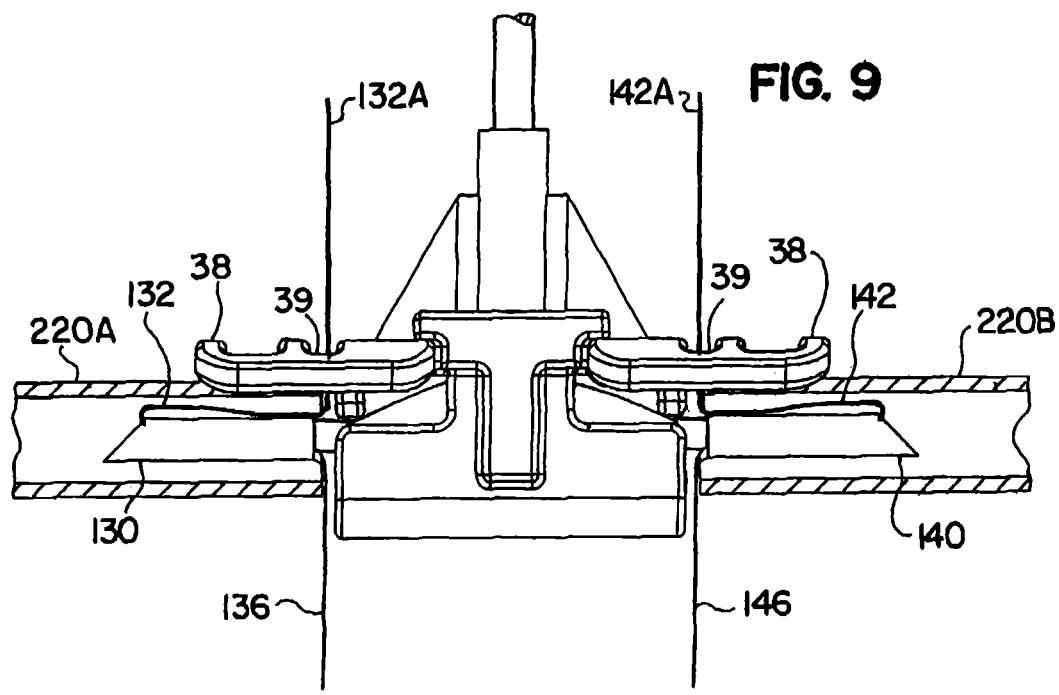
FIG. 9 is an enlarged view of the delivery device and the respective ends of the prosthesis as inserted into the vessel end portions of FIG. 8, prior to expansion of the prosthesis.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. It is understood that like-referenced numerals are used throughout the Figures to designate similar components.

Throughout the specification, when referring to a medical device, or a portion of a medical device, the terms "distal" and "distally" shall denote a position, direction, or orientation that is generally towards, or in the direction of, the patient when the device is in use. The terms "proximal" and "proximally" shall denote a position, direction, or orientation that is generally away from the patient, or closer to the operator, during use of the device.

The delivery device described herein can deploy a prosthesis that is useful for repair of body structures that define lumens, ducts, or passageways of the body, with the term "body vessel" used in the specification to describe these structures in general, during open surgical repair. In one example, the prosthesis can be particularly useful for repair of a lacerated or transected body vessel during emergency open surgery, and particularly, to obtain hemostasis or fluid stability while maintaining blood perfusion or fluid flow. While some prosthetic devices are only implanted temporarily for treatment, a prosthesis as further described herein can be implanted permanently by utilizing the delivery device described herein, thereby obviating the need for further surgical intervention and repair. The prosthesis can be secured in a rapid manner during emergency surgery without the use of a ligature or suture placed around the vessel. In another example, the prosthesis can be deployed for implantation during bypass surgery.

FIG. 1 illustrates one example of a delivery device 10 that may be utilized to deliver a prosthesis for implantation within a body vessel. Delivery device 10 includes a pair of elongated members 14, 30 movably joined to each other in known manner, such as at a pivot point 12. Elongated members 14, 30 include respective proximal ends 16, 32 and distal ends 18, 34. Proximal ends 16, 32 can include respective finger loops 17, 33 to facilitate grasping and control of the device by the operator. If desired, the proximal end of elongated members 14, 30 can also include optional cooperating members 15, 31. Conventional cooperating members 15, 31 can be provided, e.g., as spacers to maintain a distance between elongated members 14, 30, or as locking members to enable elongated members 14, 30 to be locked together, e.g., for maintaining the respective distal ends 18, 34 in a closed or otherwise fixed position. If desired, distal ends 18, 34 may have a downward curve or angle along their length distal of pivot point 12. Providing a curved distal region may enhance the ability of the operator to reach the desired portions of the vessel during implantation.

Those skilled in the art will appreciate that the general structure, composition, and configuration of delivery device 10 may be similar in some respects to that of a vascular clamp or a conventional forceps device. The elongated members 14, 30 may be formed, e.g., from a metal or metal alloy, such as stainless steel or nitinol, as well as from various plastic compositions, such as ABS and nylon. The delivery device should be provided with as small a profile as possible, in order to avoid any significant obstruction to the surgeon's view into the body opening, while at the same time allowing sufficient travel at the distal end of the device to enable the retaining members to unclamp the medical interventional device and be removed without unduly interfering with the interventional device, as further described herein.

Distal end 18 of elongated member 14 terminates at distal tip 19. Distal end 34 of elongated member 30 terminates at distal tip 35. A retaining member suitable for receiving and retaining a medical interventional device, such as a prosthesis, for implantation is provided at each distal tip. As shown in FIG. 1, retaining member 20 is provided at distal tip 19, and retaining member 36 is provided at distal tip 35. Retaining members 20, 36 are cooperatively sized and shaped to retain the prosthesis therebetween as the prosthesis is delivered to the target site. In the orientation shown in FIG. 1, the retaining members 20, 36 are spaced in an open position.

Retaining members 20, 36 may be more clearly observed in FIGS. 2 and 3. FIG. 2 is an enlarged view of the distal end of delivery device 10, illustrating the retaining members 20, 36 in the position as shown in FIG. 1. FIG. 3 is another enlarged view of the distal end of delivery device 10, wherein retaining members 20, 36 are rotated 180 degrees from the orientation of FIGS. 1 and 2.

In each of the rotational orientations shown in FIGS. 2 and 3, each retaining member is spaced from the other retaining member a distance that approximates the open position of device 10 illustrated in FIG. 1. In this example, retaining member 36 comprises a generally rigid wall member 37 having a pair of wings 38 projecting in a transverse direction therefrom. Each wing 38 preferably includes at least one aperture 39 or corresponding element for receiving a tab of a splittable sheath, as further described herein. The presence of the apertures also allows the user to view the vessel as the end of the prosthesis is inserted therein. Wall member 37 also includes a generally cylindrical portion 40 having a bore therein for receiving distal tip 35 of elongated member distal end 34. Retaining member 36 may also include one or more appendages, such as arms 42, ledge 44, and ribs 45. A respective arm 42 may be positioned along an underside of each wing 38, and ledge 44 may be provided along the bottom portion of retaining member 36. Together, arms 42 and ledge 44 assist in the alignment of the prosthesis in the delivery device, as further shown in FIGS. 6, 9, and 10. When present, ribs 45 provide strength and support to retaining member 36.

In the referenced example, retaining member 20 comprises generally rigid cradle member 21. Retaining member 20 includes a generally cylindrical portion 24 having a bore therein for receiving distal tip 19 of elongated member distal end 18. Cradle member 21 may include one or more appendages for aligning the prosthesis when positioned in the delivery device. In the example shown, the appendages may include arms 26, ledge 28, and one or more ribs 29, 29'. As shown in the figures, the respective arms 26, 42 and ledges 28, 44 of retaining members 20, 36 are cooperatively sized and spaced to retain the prosthesis when the delivery device is in a closed position prior to deployment at the target site. When present, ribs 29 in contact with cylindrical portion 24 add reinforcement to the cylindrical portion. Rib 29' provides strength and support to retaining member 20. In addition to providing structural support, ribs 45 and 29' may be arranged to interact with each other when clamped over the prosthesis to grip the prosthesis and inhibit it from sliding transversely when the tabs of the sheath are pulled, as described herein.

Retaining members 20, 36 may be formed in any conventional manner, such as by injection molding. Some examples of suitable compositions of the retaining members include ABS, nylon, polyurethane, polypropylene, and polycarbonate. The retaining members then may be engaged with respective distal tips 19, 35 in any conventional manner, such as via adhesion as the distal tips 19, 35 are received in respective retaining member bores 24, 40. Alternatively, the retaining members may be insert molded directly over tips 19, 35 of elongated members 14, 30, respectively. In another example, the retaining members may be formed from metal or metal alloys (casting and sintering), and welded, riveted, screwed, or crimped onto the delivery device in known fashion.

FIG. 4 illustrates one example of a prosthesis 100 that may be deployed at the target site via delivery device 10. Prosthesis 100 may be a conventional stent/graft device of the type known for implantation in a body vessel. In the example shown, prosthesis 100 includes stent 106 overlying graft body 110. One or more anchoring members, such as barbs 120, are generally provided along the prosthesis, typically along the proximal and distal ends 102, 104 of the prosthesis, for anchoring the prosthesis in the body vessel. The anchoring members may be configured to radially extend from the stent a suitable distance and at a suitable angle for anchoring the prosthesis in the tissue of the vessel.

Those skilled in the art will appreciate that many examples of prostheses suitable for use herein are known in the art. Some examples of suitable prostheses are described in U.S. Patent Application Publications 2012/0035708 and 2012/0035706, incorporated herein by reference in their entireties. As stated above and as shown in the incorporated-by-reference documents, the prosthesis can include a generally tubular graft body and/or one or more anchoring members and/or supporting members (e.g., stents) together defining a fluid passageway. The prosthesis is expandable between a radially compressed, delivery configuration, and a radially expanded, deployed configuration (FIG. 4). Preferably, the prosthesis is self-expandable, that is, it is capable of expansion upon removal of an outer constraining member without the necessity of additional mechanical means to effect such expansion, such as an inflatable balloon. Such self-expandable prostheses are well known in the medical arts, and examples of such are provided in the incorporated-by-reference documents. If desired, a mechanically expandable prosthesis may be utilized in some applications.

The anchoring members and/or supporting members can be attached to the graft body by sutures sewn therein, wire, staples, clips, bonding agents, or other methods that are known for achieving a secure attachment to the graft body. The prosthesis has a size and shape suitable for at least partial placement within a body vessel, such as an artery or vein, and most particularly, for placement at the site of a vascular trauma. The prosthesis may be easily manipulated during delivery to a body vessel such as a transected artery or vein during emergency surgery, and particularly, to obtain hemostasis while maintaining blood perfusion.

The supporting member can be any stent pattern known to one skilled in the art. Examples of stent patterns include the Z-STENT® and ZILVER® stent, each available from Cook Medical Incorporated, of Bloomington, Ind. The anchoring member and/or supporting member can be formed of a biocompatible metal known in the art for such use, such as stainless steel (e.g., 316L SS), titanium, tantalum, nitinol or other shape memory materials, or a high-strength polymer. Preferably, the anchoring member can provide vessel fixation, while avoiding adverse conditions such as pressure induced necrosis of the medium muscular arteries of the type that may result from tying ligatures circumferentially around a connector or a vascular conduit. As stated above, the supporting member can comprise one or more stents 106. The anchoring members can include barbs 120, as well as various alternative structures, such as fibers, bristles, or outer protruding and penetrable media. Stents and other supporting structures having anchoring members suitable for engagement with a vessel wall are well known in the medical arts.

The graft body 110 can be formed from conventional materials well known in the medical arts. The graft body may comprise an expanded polytetrafluoroethylene (ePTFE), polytetrafluoroethylene, silicone, polyurethane, polyamide (nylon), as well as other flexible biocompatible materials. The graft body can also be formed from known fabric graft materials such as woven polyester (e.g. DACRON®), polyetherurethanes such as THORALON® from Thoratec Corporation (Pleasanton, Calif.), polyethylene such as an ultra-high molecular weight polyethylene (UHMwPE), commercially available as DYNEEMA®. The graft body may also comprise a bioremodelable material as further described in the incorporated-by-reference documents.

Although the examples shown herein illustrate one or more stents positioned on an outer surface of a graft body, this arrangement may be reversed. That is, the stent structure may be positioned interiorly of the graft body. In some embodiments, a stent structure may be positioned both interiorly and exteriorly of the graft body. In still further embodiments, one or more stents may be encapsulated within the graft body.

FIG. 5 illustrates the prosthesis 100 in a condition for deployment. Each end 102, 104 of the prosthesis is constricted and maintained in a respective splittable sheath 130, 140. An intermediate length 105 of prosthesis 100 between proximal and distal ends 102, 104 is not constrained. Those skilled in the art will appreciate that prosthesis 100 has a length suitable for bridging a damaged area of tissue in the body vessel, as further described herein. For example, a prosthesis may have a length between about 40 and 100 mm, and more typically, between about 50 and 70 mm. With a prosthesis of about 50 to 70 mm, approximately 10-12 mm at each axial end of the prosthesis is sheathed and inserted into a respective vessel end.

Many suitable examples of splittable sheaths for maintaining a prosthesis, such as prosthesis 100, in a constricted, or compressed, condition prior to deployment at the target site are known in the art. As stated above and as shown in FIG. 5, a separate splittable sheath constrains each end of the prosthesis. Sheaths 130, 140 can be made of any material that is biocompatible and suitable for retaining the prosthesis ends 102, 104 in the radially constricted condition, and yet still capable of being split and/or peeled from the prosthesis in known fashion. It is desirable that the sheath is made from materials that are as thin as possible to reduce the overall delivery profile of the system.

The sheath can be configured to be separated, preferably longitudinally, along a relatively predictable path. The material of the sheath is configured to be split or cut into two or more portions by movement of the sheath tab 132, 142 relative to the prosthesis. This action opens a fissure along the length of the sheath that permits removal of a split portion of the sheath from the prosthesis. A predetermined split line may be formed in the sheath through which the tear or split progresses due to properties of, and/or features incorporated into the material. In one example, the sheath can comprise a splittable polymer such as a molecularly oriented PTFE of a type commonly utilized in splittable sheaths, such as the PEEL-AWAY® Introducer Sheaths commercially available from Cook Medical Incorporated. Splittable sheaths are described, e.g., in U.S. Pat. No. 4,306,562 to Osborne and U.S. Pat. No. 4,581,025 to Timmermans, each of which is incorporated herein by reference in its entirety. The sheath can include one or more pre-weakened features, such as a score line, perforations, or reduced wall thickness regions, extending longitudinally along the length of the sheath to provide for controlled splitting of the sheath along a relatively predictable pathway.

In the example shown, each of the splittable sheaths 130, 140 includes a separate tab 132, 142 at an end thereof. Typically, tab 132, 142 is positioned at the end of the respective sheath 130, 140 farthest from the intermediate length 105 of the prosthesis, as shown in FIG. 5. Sheath 130, 140 may also include a second tab 136, 146 along the radially opposite side of sheath from tab 132, 142. Typically, tab 136, 146 is positioned at the end of the respective sheath closest to the intermediate length 105 of the prosthesis. Tabs 136, 146 are provided to facilitate removal of the lower portions of the sheath following a splitting and removal of the upper portions, as further described herein.

FIG. 6 illustrates prosthesis 100 loaded into delivery device 10. Respective sheaths 130, 140 are positioned to constrict the proximal and distal ends 102, 104 of the prosthesis. As explained above, retaining members 20, 36 are in the open, or spaced, position as shown in FIGS. 1-3 when the prosthesis and sheaths are loaded into the delivery device. Once the prosthesis and sheaths have been loaded into delivery device 10, retaining members 20, 36 are maneuvered into the closed position shown in FIG. 6. The retaining members may be easily maneuvered between the open and closed positions by manipulating the respective finger loops 17, 33, or analogous structure, provided along the proximal ends 16, 32 of the delivery device in well-known fashion. Preferably, an end 132A, 142A of each of tabs 132, 142, is threaded through an aperture 39 of a respective wing 38 of retaining member 36, as shown in FIGS. 6 and 9.

Use of delivery device 10 for deploying a prosthesis at a target site is described with reference to FIGS. 7-10. FIG. 7 depicts one example of a body vessel for deployment of a prosthesis, in this case a body vessel 220 in the leg of a patient. The body vessel 220 has previously been subjected to a traumatic episode, resulting in a portion 222 of body vessel 220 being torn away or otherwise severely damaged. Pre-surgery preparation has been applied to the leg and a trauma pathway has been formed therein in order to gain direct, open air, access to the body vessel and the damaged portion thereof. After clamping the body vessel 220 on both ends of the portion 222 to restrict blood flow temporarily, the body vessel 220 can be cut or transected by the clinician into two end portions 220A, 220B, as shown in FIG. 8. The transection may be at the damaged portion 222 of the blood vessel 220, and extend as far away as necessary from the damaged portion to remove unhealthy and/or unrepairable portions of the body vessel.

A prosthesis 100 is selected to have a length sufficient to bridge the laceration in the vessel or the gap between the body vessel portions 220A, 220B, and a radial expanded cross-section sufficient to engage the inner walls of the body vessel portions. Prosthesis 100 having sheath portions 130, 140 in place at the respective distal ends of the prosthesis (FIG. 5) is loaded into delivery device 10. If desired, delivery device 10 may be supplied with a prosthesis of a desired length/diameter pre-loaded into the delivery device. As shown in FIG. 6 and as described above, prosthesis 100 is captured between retaining members 20, 36 which have been maneuvered into the closed position as shown.

The distal end of delivery device 10 having the prosthesis loaded therein is maneuvered into the damaged leg portion shown in FIG. 8 through an open air opening of the type shown in FIGS. 7, 8. The respective ends of the prosthesis covered by sheaths 130, 140 are inserted into respective vessel ends 220A and 220B. Typically, the ends are inserted to the maximum distance allowed by the retaining members (FIG. 9). In this event, the anchoring members of the prosthesis are in position to engage the tissue upon expansion of the prosthesis. The vessel portion 220A may be manually pulled over the first sheath 130. The delivery device 10 and the prosthesis 100 can then be manipulated in order to introduce second sheath 140 into the vessel portion 220B by a sufficient distance for the purposes of engagement and/or anchoring.

Respective ends 132A, 142A of tabs 132, 142 are pulled to split the underlying sheath 130, 140. For vessels at a lesser depth in the leg, the ends 132A, 142A may be accessible to the physician. In this instance, the tabs may be pulled by hand. For deeper vessels, a needle holder or like device may be used to pull the respective tabs in known fashion. Alternatively, a respective prosthesis end can be inserted into either vessel portion 220A or 220B, and the tab associated with that prosthesis end can be pulled. Then the opposite end of the prosthesis can be inserted into the other vessel end and its tab can be pulled. In this example, the anchoring members on the first end will keep the prosthesis engaged with the vessel end during manipulation to insert/deploy the second end. Since the vessels are elastic, they are often stretched slightly in order to properly engage the prosthesis. In some cases, it may be difficult to keep both vessel ends in position over the sheaths prior to pulling the tabs, and thus, the sequential insertion as described may be advantageous.

Figure 10:
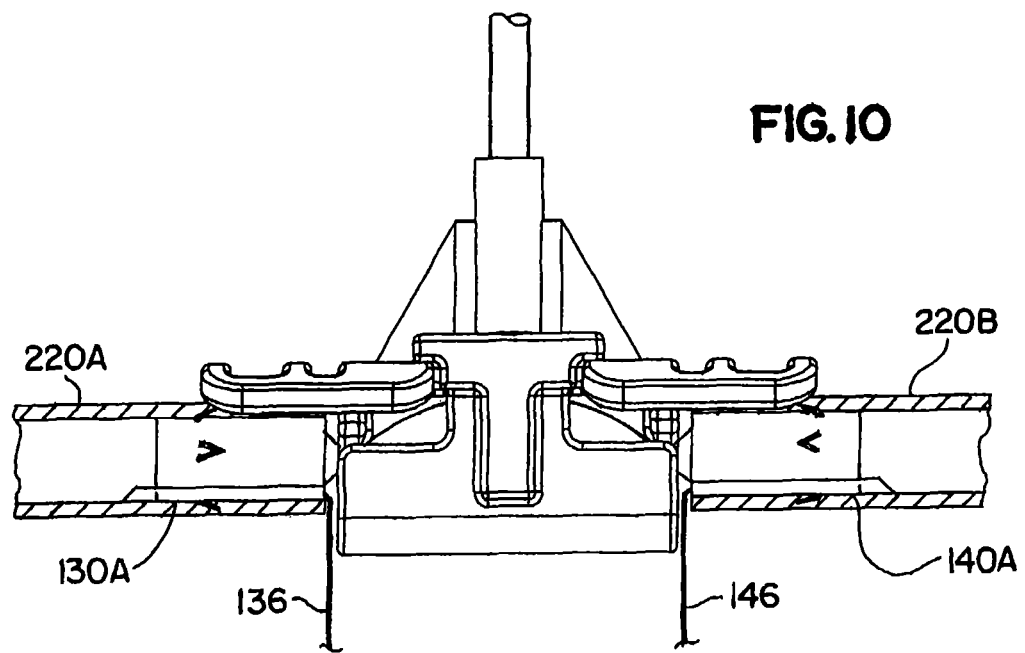
FIG. 10 illustrates the delivery device and respective prosthesis ends following splitting of the sheath and expansion of the prosthesis.

As tabs 132, 142 are pulled from the vessel, a split portion of sheath 130, 140 engaged with tab 132, 142 is likewise removed. Once relieved from the constraints imposed by sheaths 130, 140, prosthesis distal ends 102, 104 self-expand to the interior diameter of the vessel, as shown in FIG. 10. In one variation, the prosthesis ends may be sized to expand to a diameter slightly greater (e.g., about 1-2 mm greater) than the interior diameter of the vessel, thereby causing the vessel to stretch slightly. This increases the likelihood of creating a secure engagement between the anchoring members with the interior vessel wall, and also minimizes the likelihood of blood leakage upon restoration of blood flow through the vessel. The needle holder may be maneuvered to grasp tabs 136, 146 and thereby remove a remaining portion of sheaths 130A, 140A.

Once the respective prosthesis ends have been inserted into the vessel ends as described, the retaining members can be opened to free the prosthesis, and the delivery device can be removed from the surgical site.

Figure 11:
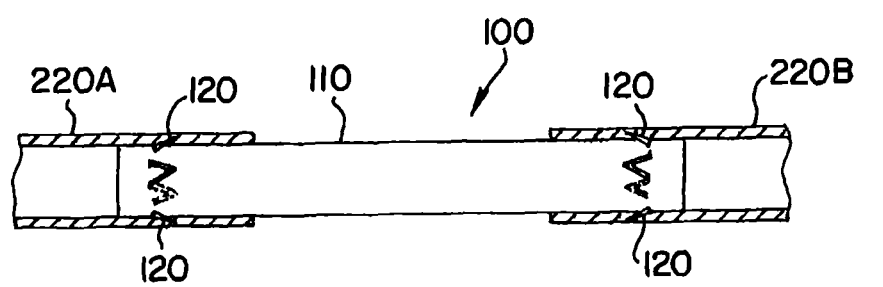
FIG. 11 illustrates the prosthesis deployed in the vessel in an expanded condition following removal of the sheaths.

Upon self-expansion of the prosthesis, barbs 120 engage the interior vessel wall, as shown in FIG. 11. Barbs 120 may be provided in a circumferential ring-like pattern around the prosthesis as shown, or may be provided in a more random pattern. In another alternative, two or more rows of barbs may be provided along each end of the prosthesis. Stent 106 is not shown in this figure, to better illustrate the barbs. In addition, in some embodiments graft body 110 may overlie the stent, such that the stent would not be visible. As shown, the prosthesis 100 is fully deployed and expanded to interconnect the first and second vessel portions 220A, 220B of the body vessel 220 to form a conduit, e.g., for blood flow. As stated, prosthesis 100 can be adapted for permanent placement within the patient, thereby obviating a need for subsequent surgical intervention. Once the prosthesis is in place and all portions of the sheath have been removed, blood flow is restored by unclamping or untying each end of the vessel.

Although the device has been described in connection with its primary intended use for repair of vascular trauma, those skilled in the art will appreciate that the device may also be used to repair other traumatic conditions, such as trauma in other body vessels and cavities, as well as during bypass surgery.

It is therefore intended that the foregoing detailed description be regarded as illustrative rather than limiting, and that it be understood that it is the following claims, including all equivalents, that are intended to define the spirit and scope of this invention.

The invention claimed is:

1. A system for open surgical repair of a damaged wall portion of a body vessel, comprising:
    a prosthesis having a first end and a second end, said prosthesis being expandable from a constricted condition wherein at least said first and second ends have a diameter less than a diameter of the body vessel at said damaged wall portion, to an expanded condition wherein said prosthesis ends engage an interior surface of said body vessel;
    a first splittable sheath for maintaining said prosthesis first end in said constricted condition, and a second splittable sheath for maintaining said prosthesis second end in said constricted condition, each of said first and second sheaths having a first tab extending therefrom and being configured for splitting upon a withdrawal of said first tab, such that said respective prosthesis end is expandable from said constricted condition to said expanded condition; and
    a device for delivery of said prosthesis to said damaged wall portion, the device comprising first and second generally elongated members, each elongated member having a proximal end accessible to an operator, and a distal end, said elongated members joined at a pivot point such that said distal ends are maneuverable between a closed position for retaining said prosthesis during delivery to said damaged wall portion and an open position for releasing said prosthesis upon deployment at said damaged wall portion; said first elongated member having a first retaining member disposed at said first elongated member distal end, and said second elongated member having a second retaining member disposed at said second elongated member distal end; said first and second retaining members configured for retaining said prosthesis therebetween in said constricted condition for insertion through said damaged wall portion when said distal ends are arranged in said closed position, wherein said first retaining member comprises a wall having a pair of members projecting therefrom, a first of said pair of projecting members including a first opening therein receiving the first tab extending from the first splittable sheath, and the second of said pair of projecting members including a second opening therein receiving the first tab extending from the second splittable sheath.

2. The system of claim 1, wherein said prosthesis includes one or more anchoring members at said first and second ends, said anchoring members configured for anchoring said prosthesis ends in said body vessel.

3. The system of claim 2, wherein said prosthesis comprises a supporting structure having a graft body disposed along a surface of the supporting structure.

4. The system of claim 2, wherein said prosthesis has a length of about 50 to 70 mm.

5. The system of claim 4, wherein each of said first and second prosthesis ends maintained in a respective sheath has a length between about 10 and 12 mm.

6. The system of claim 1, wherein the second retaining member comprises one or more members maneuverable in conjunction with the first retaining member for aligning the prosthesis in said device in said constricted condition.

7. The system of claim 6, wherein each of said first and second retaining members comprises at least one rib, the ribs of the first and second retaining members configured to cooperatively grip said prosthesis therebetween for inhibiting lateral movement of said prosthesis when said elongated member distal ends are arranged in the closed condition.

8. The system of claim 7, wherein each of the first and second splittable sheaths includes a second tab, wherein a first portion of each of said first and second splittable sheaths is removable upon withdrawal of said first tab, and a second portion of each said first and second splittable sheaths is removable upon withdrawal of said second tab.

* * * * *